(12) United States Patent
Bobbitt et al.

(10) Patent No.: US 10,420,808 B2
(45) Date of Patent: Sep. 24, 2019

(54) SEAWEED EXTRACT AND COMPOSITION USEFUL AGAINST CANCER CELLS

(71) Applicant: OCEANS LTD., St. John's (CA)

(72) Inventors: Judith Bobbitt, St. John's (CA); Anne Mathieu, St. John's (CA); Ahmed Zein, St. John's (CA)

(73) Assignee: OCEANS LTD., St. John's (CA)

( * ) Notice: Subject to any disclaimer, the term of this patent is extended or adjusted under 35 U.S.C. 154(b) by 217 days.

(21) Appl. No.: 15/325,965

(22) PCT Filed: Jul. 17, 2015

(86) PCT No.: PCT/CA2015/050666
§ 371 (c)(1),
(2) Date: Jan. 12, 2017

(87) PCT Pub. No.: WO2016/011542
PCT Pub. Date: Jan. 28, 2016

(65) Prior Publication Data
US 2017/0165306 A1    Jun. 15, 2017

Related U.S. Application Data

(60) Provisional application No. 62/026,878, filed on Jul. 21, 2014.

(51) Int. Cl.
*A61K 36/05* (2006.01)

(52) U.S. Cl.
CPC .......... *A61K 36/05* (2013.01); *A61K 2236/00* (2013.01); *A61K 2236/33* (2013.01); *A61K 2236/333* (2013.01); *A61K 2236/51* (2013.01)

(58) Field of Classification Search
None
See application file for complete search history.

(56) References Cited

U.S. PATENT DOCUMENTS

| | | |
|---|---|---|
| 2004/0175407 A1 | 9/2004 | McDaniel |
| 2011/0110872 A1 | 5/2011 | Koganov et al. |

FOREIGN PATENT DOCUMENTS

| | | |
|---|---|---|
| EP | 2529744 A1 | 12/2012 |
| IN | 00524 | 2/2015 |

OTHER PUBLICATIONS

Nechev (Reports from the Bulgarian Science Academy (2002), vol. 55, No. 1, pp. 75-78).*
Bonati, Attilio. "Formulation of Plant Extracts Into Dosage Forms." Medicinal Plant Industry. Ed. R. Wijesekera. Baca Raton: CRC Press, 1991, 106-114.*
Sarker, Satyajit. "Natural Product Isolation." Natural Products Isolation, Second Edition. Ed. S.D. Sarker. Totowa, New Jersey: Humana Press, 2006, 1-25.*
Dembitsky, "Biogenic Iodine and Iodine-Containing Metabolites", Natural Product Communication, 2006, vol. 1, No. 2, pp. 139-175.
Horincar, et al "Evaluation of bioactive compounds in extracts obtained from three romanian marine algae species", ACRomanian Biotechnological Letters, University of Bucharest, 2011, vol. 16, No. 6, pp. 71-78.
Farasat, et al, "Antioxidant Properties of Some Filamentous Green Algae (*Chaetomorpha* Genus)", Brazilian Archives of Biology and Techology, 2013, vol. 56, No. 6, pp. 921-927.
De Lara-Isassi, et al, "Nuevas adiciones al conocimiento de la actividad antibiotica de macroalgas marinas mexicanas", Hidrobiologica, 1999, vol. 9, No. 2, pp. 159-169 (English abstract attached).
Salvador, et al, "Antimicrobial activity of Iberian macroalgae", Scientia Marina, 2007, vol. 71, No. 1, pp. 101-113.
Sivakumar, et al, "Isolation and screening of bioactive principle from Chaetomorpha antennina against certain bacterial strains", Saudi Pharmaceutical Journal, 2013, vol. 21, pp. 119-121.
Yuan, et al, "Antioxidant and antiproliferative activities of extracts from a variety of edible seaweeds", Science Direct, Food and Chemical Toxicology, 2006, vol. 44, pp. 1144-1150.
De Seve, et al, "Les Algues Marines Benthiques des Iles-de-la-Madeleine", Proc. N.S. Inst. Sci, 1979, vol. 29, pp. 223-233 (English abstract attached).
Kim, et al, "Anticancer Compounds from Marine Macroalgae and Their Application as Medicinal Foods", Advances in Food and Nutrition Research, 2011, vol. 64, pp. 213-224.
Schiewer, "Auxinvorkommen und Auxinstoffwechsel bei mehrzelligen Ostseealgen I. Zum Vorkommen von Indol-3-Essigsäure [Occurrence and metabolism of auxin in multicellular algae of the Baltic Sea: On the occurence of indole-3-acetic acid]", Planta (Berl.), vol. 74, 1967, pp. 313-323 (English abstract attached).
Nechev, et al., "Phospholipid composition and antioxidative activity of algae from the Bulgarian coast", Reports From The Bulgarian Science Academy, vol. 55, issue 1, Jan. 1, 2002, pp. 75-78.

* cited by examiner

*Primary Examiner* — Susan Hoffman
(74) *Attorney, Agent, or Firm* — Hovey Williams LLP

(57) ABSTRACT

The present invention provides a crude extract and fractions from the seaweeds *Chaetomorpha Cannabina* (CC) or *Cladophora sericea* (CS), method of preparation and its use for inhibiting the growth of cancer cells.

17 Claims, 6 Drawing Sheets

SEAWEED EXTRACT AND COMPOSITION USEFUL AGAINST CANCER CELLS

RELATED APPLICATIONS

This application is the National Stage of International Patent Application No. PCT/CA2015/050666, filed Jul. 17, 2015, which is hereby incorporated by reference in its entirety, and which claims priority to U.S. Provisional Patent Application No. 62/026,878, filed Jul. 21, 2014.

FIELD OF THE INVENTION

The present invention relates to extracts from the seaweed *Chaetomorpha Cannabina* (CC) or *Cladophora sericea* (CS), method of preparation and use for inhibiting the growth of cancer cells.

BACKGROUND OF THE INVENTION

Cancer is a disease that seriously jeopardizes the health of human beings. Around the globe, about 6 millions people die of cancer every year, with another 10 millions seriously affected by the disease. According to the estimate of the World Health Organization, in the 21st century, cancer will become the "number one killer" of mankind.

In the past several decades, many ways of treating cancer became available, mainly including surgery, radiotherapy, chemotherapy, hormonotherapy, gene therapy, and immunotherapy, among which surgery, radiotherapy and chemotherapy have become the major means. Chemotherapy refers to treating cancer with chemical medication. It is the most rapidly expanding field in the diagnosis and treatment of cancer. A great number of new medicines aiming at different targets are ready for clinical application, and developments in research in mechanism of drug action and pharmacokinetics have made the clinical administration routes and means more fitting for killing tumor cells while protecting the normal tissues.

The search for natural-derived molecule for inhibiting cancer cells has led to the discovery of molecules such as Taxol or Vinblastine. Despite the utility of *taxus* and *vinca* alkaloids in the clinic, there are serious limitations to these therapies.

One major drawback when treating cancer is to achieve selectivity against this type of cancer cells.

There remains a need to discover and isolate new potent compounds having selective activity against certain types of cancer cells, thereby providing highly selective anti-cancer molecules.

Under such a background, a novel cancer cell inhibiting extract is highly desirable.

SUMMARY OF THE INVENTION

A main aspect intended to be addressed by the present invention is to provide a novel extract from the seaweed *Chaetomorpha Cannabina* (CC).

Another main aspect intended to be addressed by the present invention is to provide a novel extract from the seaweed *Cladophora sericea* (CS).

According to a first aspect of the present invention, there is provided a *Chaetomorpha Cannabina* (CC) or *Cladophora sericea* (CS) solvent extract defined by NMR peaks at about 5.4; about 2.8-2.9; and about 2.0-2.3.

According to a further aspect, the present invention provides a composition comprising the extract as defined herein, in admixture with a physiologically acceptable excipient.

According to a further aspect of the present invention, there is provided use of the extract as defined herein for inhibiting growth of cancer cells.

According to a further aspect of the present invention, there is provided use of the extract as defined herein for the manufacture of composition for treating cancer in a mammal.

According to a further aspect, the present invention provides use of the composition as defined herein for the treatment of cancer in a mammal.

According to a further aspect, the present invention provides a method for obtaining an extract from *Chaetomorpha Cannabina* (CC) or *Cladophora sericea* (CS) seaweed, comprising the steps of:

a) mixing material from said seaweed with a solvent to obtain a solvent:material mixture;

b) separating a solid fraction and a liquid fraction from said mixture, said liquid fraction forming said extract from said seaweed material.

According to a further aspect, the present invention provides a method for inhibiting growth of cancer cells comprising contacting said cell with a growth-inhibiting concentration of the extract or the composition as defined herein.

According to a further aspect, the present invention provides a method for treating cancer in a mammal comprising administering a growth-inhibiting concentration of the composition as defined herein to the mammal.

DETAILED DESCRIPTION OF THE INVENTION

ABBREVIATIONS AND DEFINITIONS

Figure 1:
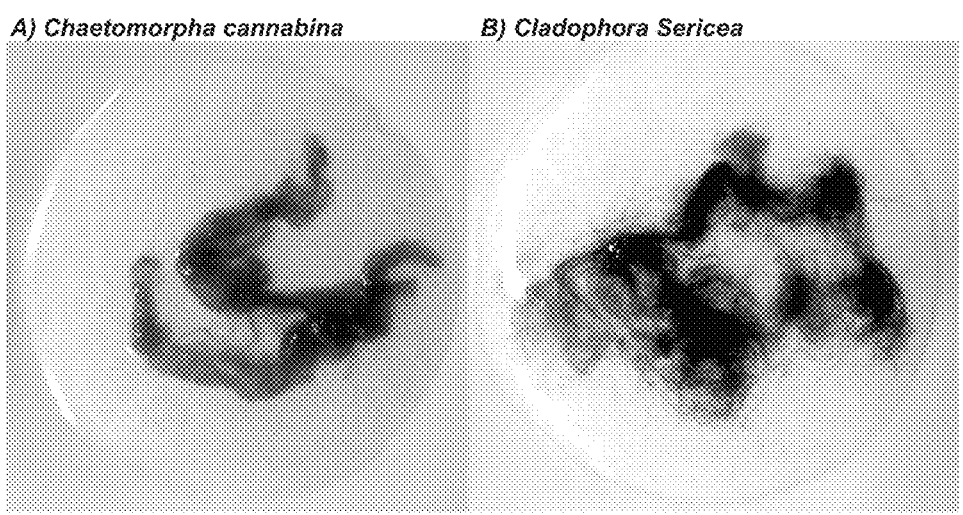
FIG. 1. Pictures of seaweeds: A) *Chaetomorpha Cannabina* (CC) and B) *Cladophora sericea* (CS) samples.

Abbreviations bis-AAF-R110: bis-alanyl-alanyl-phenylalanyl-rhodamine 110; CIMA: colorimetric indicative of metabolic activity; GF-AFC: Gly-Phe-7-amino-4-trifluoromethylcoumarin; HILIC: hydrophilic interaction liquid chromatography. C-18 SPE: solid phase extraction.

Definitions

The term "about" as used herein refers to a margin of + or −10% of the number indicated. For sake of precision, the term about when used in conjunction with, for example: 90% means 90%+1-9% i.e. from 81% to 99%. More precisely, the term about refer to + or −5% of the number indicated, where for example: 90% means 90%+1-4.5% i.e. from 86.5% to 94.5%.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

As used herein, the terms "disease" and "disorder" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The term "subject" or "patient" as used herein refers to an animal, preferably a mammal, and most preferably a human who is the object of treatment, observation or experiment.

"Mammal" includes humans and both domestic animals such as laboratory animals and household pets, (e.g. cats, dogs, swine, cattle, sheep, goats, horses, rabbits), and non-domestic animals such as wildlife and the like.

The term "extract" as used herein means a composition prepared by contacting solvent with seaweed material, produced following the procedures of the invention, which demonstrates inhibitory activity against one or more cancer cell line in vitro. In one aspect of the invention, an extract demonstrates inhibitory activity against cancer cell growth in vivo. As used herein, the term "extract" means an extract that is: crude, fractionated, sub-fractionated, separated, isolated, enriched or purified, without being limited thereto.

The term "isolated" is used herein to indicate that the protein exists in a physical milieu distinct from that in which it occurs in nature. For example, the isolated molecule may be substantially isolated (for example enriched or purified) with respect to the complex cellular milieu in which it naturally occurs, such as in a crude extract. When the isolated molecule is enriched or purified, the absolute level of purity is not critical and those skilled in the art can readily determine appropriate levels of purity according to the use to which the material is to be put. In some circumstances, the isolated molecule forms part of a composition (for example a more or less crude extract containing many other substances) or buffer system, which may for example contain other components. In other circumstances, the isolated molecule may be purified to essential homogeneity, for example as determined spectrophotometrically, by NMR or by chromatography (for example LC-MS).

The term "crude" means compounds or molecules that have not been entirely separated from the components of the original composition in which it was present. Therefore, the terms "separating", "purifying" or "isolating" refers to methods by which one or more components of the biological sample are removed from one or more other components of the sample.

The extracts described herein can be formulated as pharmaceutical compositions by formulation with additives such as pharmaceutically acceptable excipients, pharmaceutically acceptable carriers, and pharmaceutically acceptable vehicles, or as nutraceutical or nutritional formulations with additives such as nutraceutically or nutritionally acceptable excipients, nutraceutically or nutritionally acceptable carriers, and nutraceutically or nutritionally acceptable vehicles.

As used herein, the term "pharmaceutically acceptable" refers to molecular entities and compositions that are physiologically tolerable and do not typically produce an allergic or similar unwanted reaction, such as gastric upset, dizziness and the like, when administered to human. Preferably, as used herein, the term "pharmaceutically acceptable" means approved by regulatory agency of the federal or state government or listed in the U.S. Pharmacopeia or other generally recognized pharmacopeia for use in animals, and more particularly in humans.

The term "carrier" refers to a diluent, adjuvant, excipient, or vehicle with which the compounds of the present invention may be administered. Sterile water or aqueous saline solutions and aqueous dextrose and glycerol solutions may be employed as carrier, particularly for injectable solutions. Suitable pharmaceutical carriers are described in "Remington's Pharmaceutical Sciences" by E. W. Martin.

The extracts and compositions of the present invention can be prepared as nutritional formulations such as foods, including medical or functional foods and dietary supplements. A "medical or functional food" is defined as being consumed as part of a usual diet but which has been demonstrated to have physiological benefits and/or to reduce the risk of a disease or condition such as a chronic disease, beyond basic nutritional functions. A "dietary supplement" is defined as a product that is intended to supplement the human diet and is typically provided in the form of a pill, capsule, tablet, or like formulation. By way of example, but not limitation, a dietary supplement may include one or more of the following ingredients: vitamins, minerals, herbs, botanicals, amino acids, dietary substances intended to supplement the diet by increasing total dietary intake, and concentrates, metabolites, constituents, extracts or combinations of any of the foregoing. Dietary supplements may also be incorporated into food stuffs, such as functional foods designed to promote health or to prevent disease or disorders. If administered as a medicinal preparation, the composition can be administered, either as a prophylaxis or treatment, to a patient in any of a number of methods. The subject compositions may be administered alone or in combination with other pharmaceutical agents and can be combined with a physiologically acceptable carrier thereof. The effective amount and method of administration and aim of the particular formulation can vary based on the individual subject, the stage of the disease or condition, and other factors evident to one skilled in the art. In the case of a pharmaceutical formulation as well as a nutraceutical formulation, during the course of the treatment, the concentration of the subject compositions may be monitored (for example, blood plasma levels may be monitored) to insure that the desired level is maintained.

The term "nutraceutical" has been used to refer to any substance that is a food or a part of a food and provides medical or health benefits, including the prevention and treatment of disease or condition. Thus, a nutraceutical is a product isolated or purified from foods that is generally sold in medicinal forms not usually associated with foods. A nutraceutical is demonstrated to have a physiological benefit or provide protection against chronic disease. Hence, compositions falling under the label "nutraceutical" may range from isolated nutrients, dietary supplements and specific diets to genetically engineered designer foods, herbal products, and processed foods such as cereals, soups and beverages. In a more technical sense, the term has been used to refer to a product isolated or purified from foods, and generally sold in medicinal forms not usually associated with food and demonstrated to have a physiological benefit or provide protection against chronic disease. Suitable nutraceutically acceptable excipients may include liquid solutions such as a solution comprising a vegetable- and/or animal- and/or fish-derived oil.

DETAILED DESCRIPTION OF PARTICULAR ASPECTS OF THE INVENTION

Solvent Extracts

With the aim of providing an alternative source of anti-cancer molecules, there is provided a crude solvent extract from the seaweed *Chaetomorpha Cannabina* (CC) or *Cladophora Sericea* (CS). Particularly, the crude extract is an organic or inorganic solvent extract. More particularly, the extract's solvent is water or alcohol; and even more particularly: aqueous alcohol.

More particularly, the crude extract is 80%, 75%, 70%, 65%, 60%, 55%, 50%, 45%, 40%, 35%, 30%, 25% aqueous alcohol extract, more particularly ethanol. Most particularly, the crude extract is an 80% aqueous ethanol extract of CC or CS.

Particularly, the crude extract is a previously hexane-defatted extract.

More particularly, the extract is a C-18 fraction of the crude extract: particularly a fraction in aqueous methanol that is 5%, 10%, 15%, 20%, 25%, 30%, 25%, 40%, 45%, 50%, 55%, 60%, 65%, 70%, 75%, 80, 85%, 90% or, 95% or 100% pure MeOH; or MeOH; $CH_2Cl_2$ (1:1). Most particularly, there is provided a C-18 fraction of the crude extract, particularly a 100% MeOH, or a 1:1 MeOH:$CH_2Cl_2$ fraction.

Extract Form

In accordance with a particular aspect of the present invention, the extract is in dried form or in solution.

Composition

In accordance with a particular aspect of the invention, there is provided a composition comprising the extract as defined herein, in admixture with a physiologically acceptable excipient.

Uses and Methods of Use

In accordance with an alternative aspect, the present invention provides the use of the extract as defined herein for inhibiting growth of cancer cells. Particularly, there is provided the use of the extract as defined herein for the manufacture of composition for treating cancer in a mammal.

In accordance with an alternative aspect of the invention, there is provided the use of the composition as defined herein for the treatment of cancer in a mammal.

In accordance with a particular aspect, the present invention provides a method of inhibiting a cancer cell growth comprising contacting said cell with a growth-inhibiting concentration of the extract as defined herein or the composition as defined herein.

More particularly, there is provided a method of treatment of cancer in a mammal comprising administering a growth-inhibiting concentration of the composition as defined herein to said mammal. Most particularly, the mammal is a pet animal or a human.

Method of Extraction

In accordance with a further aspect of the invention, there is provided a method for obtaining an extract from *Chaetomorpha Cannabina* (CC) or *Cladophora sericea* (CS), comprising the steps of:

a) mixing material from seaweed *Chaetomorpha Cannabina* (CC) or *Cladophora sericea* (CS) with a solvent to obtain a solvent:material mixture;

b) separating a solid fraction and a liquid fraction from said mixture, said liquid fraction forming said extract from said seaweed material.

Particularly, the solvent is organic or inorganic; more particularly: water or alcohol; and most particularly: aqueous ethanol. Still, most particularly, the solvent is 80% aqueous ethanol.

In accordance with an alternative aspect, the method of the invention further comprises a hexane-defatting step prior to step a).

In accordance with a particular aspect, the method further comprises the step of:

c) fractionating the extract from step b) on C-18 column with a solvent selected from the group consisting of: from 5% aq. MeOH to 100% MeOH, and 50% MeOH: $CH_2Cl_2$.

Alternatively, the method further comprises a step of drying the liquid fraction to obtain a dried extract.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Examples 1 to 10 describe *Chaetomorpha Cannabina* (CC) harvesting, extract preparation, fractionation and screening for anti-cancer activity.

Examples 10 and 11 describe *Cladophora sericea* (CS), harvesting, extract preparation, fractionation and screening for anti-cancer activity.

Example 1

Materials and Methods
Preparation of Crude Seaweed Extracts
1. Seaweed Collection and Identification A collection program for *Chaetomorpha Cannabina* was established for different geographical regions on Fortune Bay and the west coast of Newfoundland and Labrador over 2 time periods—July and September.

The general collection procedure was as follows: seaweeds were collected from the intertidal zone by hand with knives while scuba divers collected seaweed from sub tidal zones. Samples were placed in plastic sampling bags and transported to the laboratory in coolers of seawater. Upon arrival in the laboratory, each species was washed individually to remove epiphytic and extraneous matter (sand, mussels, isopods, etc.). Samples were then checked visually to ensure they were clean. If not, remaining matter was removed by hand with further washing. Seaweeds were blotted dry, weighed to the nearest g (plant wet weight) and shredded The shredded material was transferred into Erlenmeyer flasks and frozen at −60° C. until the extracts were prepared.

A representative sample of specie was also photographed (see FIGS. 1 A-B). and frozen at −20° C. for confirmation of species by Dr. Robert Hooper, a psychologist at Memorial University of Newfoundland.

2. Extract Preparation

Preparation of extracts involved freeze drying and defatting samples, followed by extraction of organic compounds with 80% aqueous ethanol.

Freeze-Drying:

Seaweeds were freeze-dried prior to extraction. This step accounts for the differences in water content among seaweeds which may otherwise affect the solubility of bioactive components. Secondary plant metabolites are also more stable when stored in a dried form. Moreover, the large scale extraction of dried plant material may cause fewer problems than extracting fresh material. In order to preserve thermolabile compounds, low temperature conditions are used throughout the process of extraction.

Erlenmeyer flasks containing the shredded seaweeds, which had been frozen at −60° C., were placed on a freeze-dryer, and lyophilized for 72-96 h at $69 \times 10^{-3}$ mbar. The weight (g) of dry material was then recorded (Plant dry weight—B, see Table 1).

Defatting of Samples:

The lipid fraction of seaweed is known to vary from 1 to 5% of the algal dry matter, which can be dominated by polyunsaturated fatty acids. Brown and red seaweeds are particularly rich in long chain polyunsaturated fatty acids such as eicosapentaenoic acid (n3, C20:5), while green seaweeds may possess levels of alpha linoleic acid (n3, C18:3). Since these polyunsaturated fatty acids are extremely susceptible to oxidation, they may result in lipid oxidation products during analysis. In order to eliminate the above oxidative processes that may have an effect on the results, samples were defatted prior to extraction of phenolic compounds.

Freeze dried seaweed samples were ground into a powder and defatted by blending the powder with hexane (1:5, w/v, 5 min) in a Waring blender at ambient temperature. Defatted samples were air-dried, vacuum packed in polyethylene pouches and kept at 4° C. until extraction.

Crude Extraction:

Different solvents or solvent systems can be used for the extraction of phenolic compounds. In general, ethanol is commonly used due to its lower toxicity compared to other solvents. Moreover, ethanol extracts have been demonstrated in many studies to have the highest antioxidant activity.

In the current study, phenolic compounds were extracted into 80% aqueous ethanol at 4° C. for 24 h. The solvent was then removed under a vacuum at 37° C. for 45 to 60 min and the resulting concentrated slurries were lyophilized for 72 to 96 h at −80° C. and $69 \times 10^{-3}$ mbar using a freeze dryer. Dry extracts were weighed (Extract dry weight in g-C, see Table 2) and stored at −60° C. until preparation for screening.

3. Extraction Yields

Extraction yields were calculated for each extract of *Chaetomorpha Cannabina* collected from different locations at different times of year. Yields ranged from 1.94 to 9.91, when expressed as g of dry extract per kg of fresh seaweed, and from 19.7 to 100.9, when expressed as g of dry extract per kg of dry seaweed (Table 1). Twenty five mg of each extract was used for anti-cancer screening.

TABLE 1

Extraction Yields

| Specimen # | Date Collected | Location | Extract dry weight (g) C | Yield C/A[a] g of dry extract/ kg of wet plant | Yield C/B[b] g of dry extract/ kg of dry plant |
|---|---|---|---|---|---|
| *Chaetomorpha Cannabina* (1) | Sep. 7, 2008 | Bonne Bay, NF | 0.42 | 3.28 | 38.18 |
| *Chaetomorpha Cannabina* (2) | Jul. 4, 2012 | Rocky Harbour, NF | 0.50 | 6.33 | 83.3 |
| *Chaetomorpha Cannabina* (3) | Sep. 17, 2012 | Bonne Bay, NF | 0.83 | 1.94 | 19.7 |
| *Chaetomorpha Cannabina* (4) | Jul. 3, 2012 | Enlish Harbour, Fortune Bay, NF | 0.39 | 3.3 | 39 |
| *Chaetomorpha Cannabina* (5) | Sep. 17, 2012 | Grand Le Pierre, Fortune Bay, NF | 3.13 | 9.91 | 100.9 |

Example 2. Primary Anti-Cancer Screening of *Chaetomorpha Cannabina* Extracts 2.1 Experimental Design Extracts Preparation:

Stock solutions of the extract (1) was prepared in dimethylsulfoxide (DMSO) at 10 mg/ml and stored in 200 μl aliquots at −20° C. until used. Working concentrations were prepared by direct dilution of the stock solution into complete culture medium. This preparation ensured that the DMSO content delivered to cells in culture never exceeded 1%.

2.2 Cell Proliferation Assay

The effects of the extracts were assessed following chronic exposure conditions in which cells were seeded at $2\times10^3$ cells/well and incubated with test compounds for 72 h. Each extract was evaluated over a range of concentrations (0, 1, 5, 10, 25, 50, or 100 µg/ml) and 50% lethal doses (LD50) established if warranted. Cell proliferation was assessed using a standard colorimetric indicator of metabolic activity (CIMA) assay. In this assay, tetrazole reduction was assessed as a measure of metabolic function by quantifying mitochondrial activity as a measure of the extent of cell proliferation within a culture. This assay is based on the reduction of yellow tetrazolium salt to purple formazan by mitochondrial reductases enzymes in viable cells, resulting in a colour change that confers a change in absorbance. This change was quantified using a spectrophotometer ($\lambda$=500-600 nm). Samples were diluted as required to ensure that values obtained with the MTT assay fell within the linear range of the protocol. Qualitative microscopic evaluation of treated cultures was used to supplement the quantitative CIMA data. Seven cell lines were employed in this study: CCD1079SK (primary human dermal fibroblast), PC3 (prostate cancer), SK-OV-3 (ovarian cancer), MCF-7 (breast cancer), U373 (astroglioma), THP-1 (acute myelogenous leukemia), and A549 (lung cancer).

2.3 Results

The results of the anti-cancer analysis are summarized in Table 2 as fold changes relative to vehicle controls. Decreased activity greater than 25% was considered significant.

Stock solutions of C.C. crude extract (#1) was prepared in dimethylsulfoxide (DMSO) at 10 mg/ml and stored in 200 µl aliquots at −20° C. until use. This preparation ensured that the DMSO content delivered to cells in culture never exceeded 1%.

CIMA Assay:

The effects of test extract was assessed following chronic exposure conditions in which cells were seeded at $2\times10^3$ cells/well (96 well plate) and incubated with test compounds for 72 h. Each fraction was evaluated over a range of eight concentrations (0, 2.5, 5, 10, 25, 50, 75 or 100 µg/ml) where sufficient material was available and 50% inhibitory concentrations ($IC_{50}$) established as warranted. Cell proliferation was initially assessed using a standard colorimetric indicator of metabolic activity (CIMA) assay. In this assay, tetrazole reduction was evaluated as a measure of metabolic function that evaluates mitochondrial activity to determine the extent of cell proliferation within a culture. This assay is based on the reduction of yellow tetrazolium salt to purple formazan by mitochondrial reductases enzymes in viable cells, resulting in a colour change that confers a change in absorbance ($\lambda$=500-600 nm). Seven human cell lines were selected for evaluation: U373 (glioblastoma-astrocytoma), A549 (lung carcinoma), PC3 (prostate adenocarcinoma), THP1 (acute monocytic leukemia), MCF7 (mammary gland adenocarcinoma), SKOV3 (ovarian adenocarcinoma) and CCD1079SK (nontransformed primary human fibroblasts) cells.

TABLE 2

Evaluation of anti-cancer activity for C.C. crude extract #1

| Conc. (µg/ml) | CCD 1079 SK Fold | Error | PC3 Fold | Error | SK-OV-3 Fold | Error | MCF-7 Fold | Error |
|---|---|---|---|---|---|---|---|---|
| 1 | 0.99 | 0.10 | 0.94 | 0.05 | 0.96 | 0.04 | 0.94 | 0.07 |
| 5 | 1.15 | 0.05 | 0.90 | 0.04 | 0.99 | 0.04 | 0.92 | 0.04 |
| 10 | 0.87 | 0.07 | 0.89 | 0.06 | 1.05 | 0.02 | 1.02 | 0.05 |
| 25 | 0.88 | 0.04 | 0.90 | 0.05 | 0.89 | 0.06 | 1.03 | 0.04 |
| 50 | *0.52*[1] | *0.03* | *0.75* | *0.03* | *0.57* | *0.03* | 1.01 | 0.04 |
| 100 | 0.46[2] | 0.02 | 0.31 | 0.05 | *0.53* | *0.02* | 0.38 | 0.07 |

| Conc. (µg/ml) | U373 Fold | Error | THP-1 Fold | Error | A549 Fold | Error | $LD_{50}$(µg/ml) |
|---|---|---|---|---|---|---|---|
| 1 | 0.91 | 0.04 | 0.99 | 0.08 | 0.87 | 0.01 | 1079SK: 78.6 |
| 5 | 0.94 | 0.04 | 0.96 | 0.02 | 0.88 | 0.02 | PC3: 81.6 |
| 10 | 0.94 | 0.01 | 0.96 | 0.04 | 0.93 | 0.04 | A549: 28.4 |
| 25 | 0.97 | 0.03 | *0.73* | *0.01* | *0.53* | *0.04* | |
| 50 | 0.87 | 0.02 | *0.62* | *0.05* | 0.31 | 0.04 | |
| 100 | *0.57* | *0.02* | *0.61* | *0.01* | 0.31 | 0.02 | |

[1] *Italics* text indicates decreased activity exceeding 25% of matched control values
[2] Bold text indicates decreased activity exceeding 50% of matched control values Example 3. Fractionation and Secondary Screening of *Chaetomorpha Cannabina* (CC) Fractions To evaluate C.C. crude extract (#1) and select fractions for biological activity in anti-cancer assay, the following was undertaken:
1) Conduct secondary bio-assay screening to confirm activity of C.C. crude extract;
2) Fractionate C.C. crude extract #1 and evaluate these fractions in biological assays;
3) Acquire information on the group of chemicals responsible for bioactivity and identify bioactive markers for standardization of extract and product formulation.

3.1 Experimental Design

Extract Preparation:

Multiplex Cytotoxicity Assay:

A multiplex cytotoxicity assay was used following the CIMA assay to further elucidate the actions of primary fractions. Cells were treated as for the CIMA assays and cells and conditioned media harvested. The multiplex assay evaluates membrane integrity as an indicator of overt cytotoxicity in cell cultures by simultaneously measuring released and cell-associated protease activity using two fluorescently-labeled protease substrates. The first, GF-AFC, is cell permeant and enters intact, live cells where it is cleaved by a cytosolic protease to emit a fluorescence signal. Decreases in this signal indicated decreased viability in a culture. The second, bis-AAF-R110, is cell impermeant and is cleaved by a cytosolic protease that is released into the culture medium by dying cells to emit a different fluorescence signal. Increases in this signal indicated increased cytotoxicity in a culture. Results were expressed as the ratio of cytotoxicity (dead cells) to viability (live cells) where values greater than 1 indicate decreased cell survival.

Figure 2:
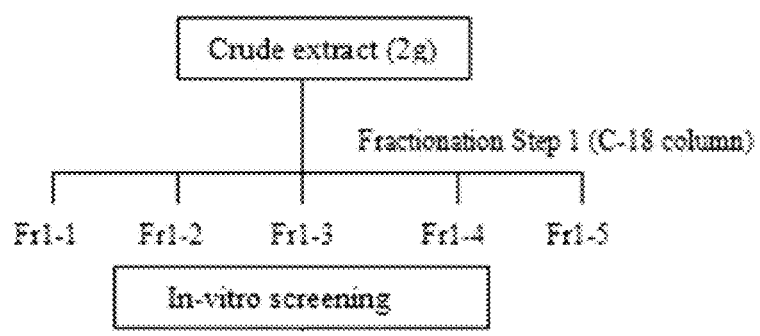
FIG. 2. Fractionation strategy for crude extracts.

Fractionation Strategy:

C.C. crude extract (#1) was fractionated as detailed in the diagram from FIG. 2. Briefly, crude extracts were initially fractionated into 5 fractions by C-18 column separation.

3.2. Results

CIMA Evaluation of Crude Extract

Figure 3:
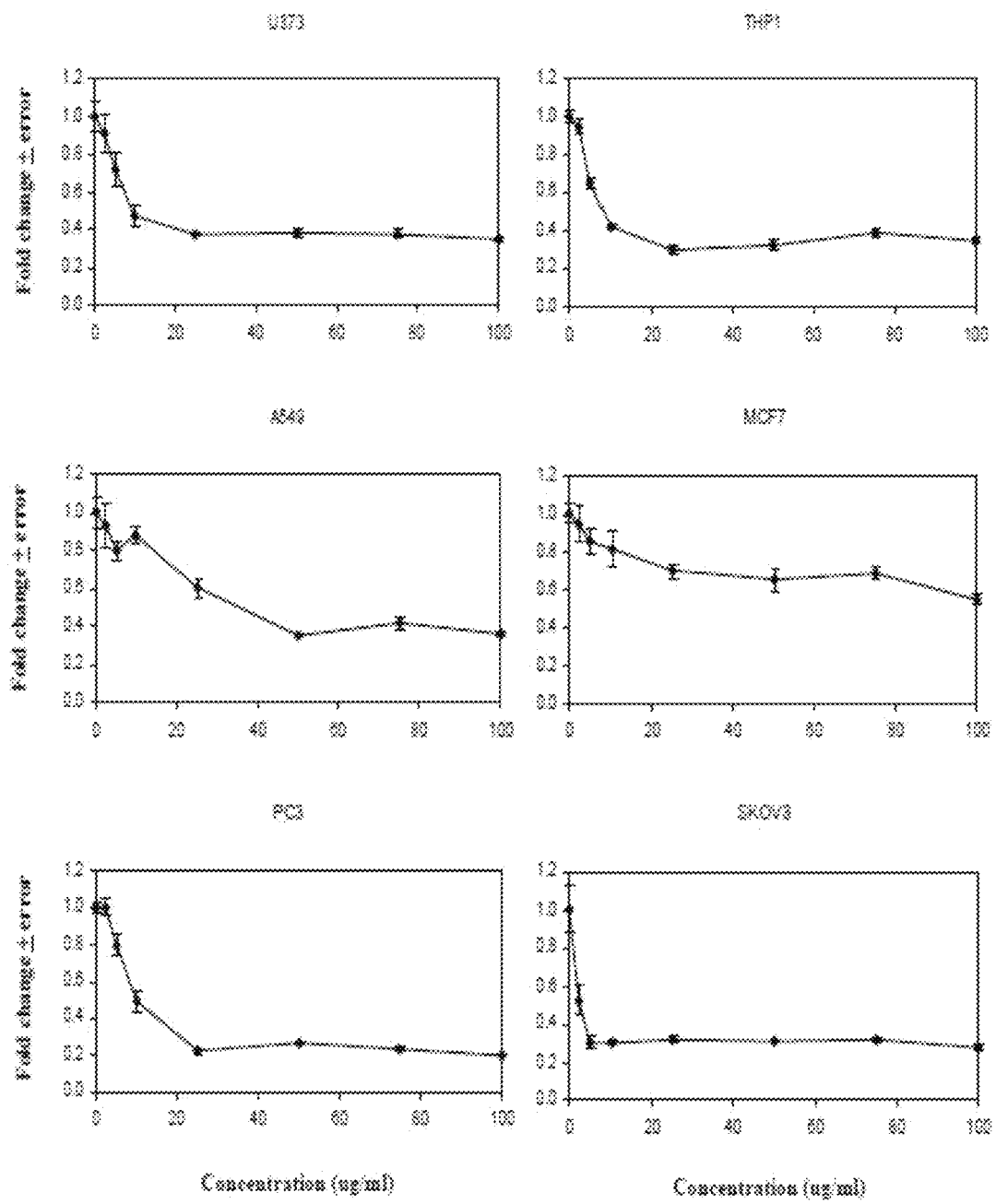
FIG. 3. Evaluation of a primary extract of CC by CIMA.

C.C. crude extract #1 exhibited high activity and $IC_{50}$ values that could be calculated. This data is summarized in Tables 3 and 4 and FIG. 3.

Evaluation of C.C. Crude Extract 1 by CIMA

Cells were seeded in 96 well plates and incubated with the indicated concentration of CC primary extract #1 for 72 h prior to CIMA assay. Equivalent concentrations of DMSO vehicle alone served as controls for each test concentration. Mean absorbance values from quadruplicate wells were expressed as percent changes relative to DMSO vehicle. Values are expressed as fold changes+relative error. Decreases exceeding 25% relative to controls were considered significant (bold). Where sufficient inhibition of cell viability/proliferation was observed to support analysis, 50% inhibitory concentrations ($IC_{50}$) are indicated in μg/ml. C.C. extract #1 was significantly active across a broad range of cell types.

TABLE 3

Evaluation of CC primary extract #1 by CIMA

| μg/ml | U373 | A549 | PC3 | THP1 | MCF7 | SKOV3 |
|---|---|---|---|---|---|---|
| 100 | −64.69 | −64.23 | −79.46 | −65.00 | −44.90 | −72.36 |
| 75 | −62.00 | −58.54 | −76.10 | −60.92 | −31.28 | −68.28 |
| 50 | −61.46 | −65.00 | −73.13 | −67.17 | −35.07 | −68.90 |
| 25 | −62.03 | −39.98 | −77.31 | −69.94 | −29.96 | −68.05 |
| 10 | −52.73 | −12.23 | −50.62 | −57.74 | −18.19 | −69.56 |
| 5 | −27.70 | −20.00 | −20.05 | −34.38 | −14.06 | −69.39 |
| 2.5 | −8.79 | −7.06 | 0.28 | −5.20 | −5.03 | −47.67 |
| 0 | 0.00 | 0.28 | 0.28 | 0.28 | 0.28 | 0.28 |
| IC50 | 9.25 | 35.00 | 9.75 | 8.50 | — | 2.75 |

Multiplex Evaluation of C.C. Crude Extract (#1)

Cells were seeded in 96 well plates and incubated with the indicated concentration of CC extract 1 for 72 h prior to multiplex analysis of cells (viability) and conditioned media (cytotoxicity). Equivalent concentrations of DMSO vehicle alone served as controls for each test concentration. Mean fluorescence values from quadruplicate wells were expressed as fold changes+relative error compared to DMSO vehicle. Decreases in viability exceeding 25% (bold) or increases in cytotoxicity exceeding 2-fold (italics) were considered significant. For analysis, results were further expressed as the ratio of cytotoxicity:viability where values exceeding 2-fold were considered indicative of decreased cell viability in the absence of overt toxicity (italics).

Figure 4:
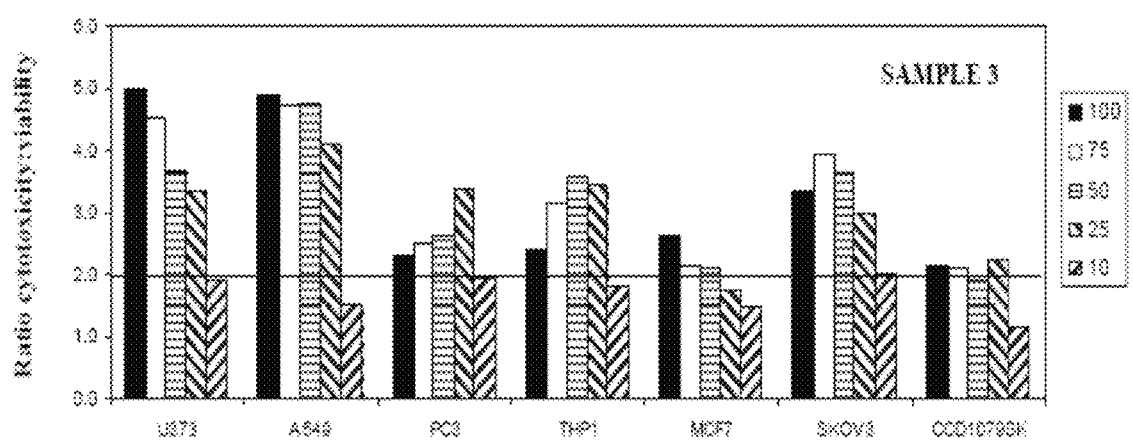
FIG. 4. Cytotoxicity: viability ratios indicative of decreased cell viability.

Consistent with the CIMA studies, the multiplex assay revealed broad spectrum decreases in cell viability for C.C. crude extract #1 (Table 4) whereas the ratios are indicated in FIG. 4. These results occurred in the absence of overt increases in cytotoxicity, suggesting that the activity of extract #1 reflected anti-proliferative potential.

TABLE 4

Multiplex evaluation of CC primary extract #1

| | μg/ml | U373 | A549 | PC3 | THP1 | MCF7 | SKOV3 | CCD1079SK |
|---|---|---|---|---|---|---|---|---|
| Viability (fold) | 100 | 0.21 | 0.14 | 0.07 | 0.13 | 0.26 | 0.21 | 0.28 |
| | 75 | 0.23 | 0.17 | 0.08 | 0.14 | 0.32 | 0.27 | 0.30 |
| | 50 | 0.24 | 0.18 | 0.09 | 0.19 | 0.35 | 0.30 | 0.34 |
| | 25 | 0.28 | 0.17 | 0.13 | 0.36 | 0.50 | 0.34 | 0.35 |
| | 10 | 0.53 | 0.72 | 0.91 | 0.88 | 0.92 | 0.57 | 0.88 |

| | μg/ml | U373 | A549 | PC3 | THP1 | MCF7 | SKOV3 | CCD1079SK |
|---|---|---|---|---|---|---|---|---|
| Viability (error) | 100 | 0.00 | 0.00 | 0.00 | 0.00 | 0.04 | 0.00 | 0.01 |
| | 75 | 0.01 | 0.00 | 0.00 | 0.00 | 0.02 | 0.03 | 0.02 |
| | 50 | 0.01 | 0.00 | 0.00 | 0.01 | 0.04 | 0.04 | 0.01 |
| | 25 | 0.02 | 0.01 | 0.01 | 0.02 | 0.04 | 0.02 | 0.02 |
| | 10 | 0.05 | 0.02 | 0.05 | 0.04 | 0.10 | 0.01 | 0.05 |

| | μg/ml | U373 | A549 | PC3 | THP1 | MCF7 | SKOV3 | CCD1079SK |
|---|---|---|---|---|---|---|---|---|
| Toxicity (fold) | 100 | 1.05 | 0.67 | 0.17 | 0.30 | 0.68 | 0.72 | 0.61 |
| | 75 | 1.06 | 0.78 | 0.20 | 0.46 | 0.69 | 1.07 | 0.63 |
| | 50 | 0.89 | 0.88 | 0.22 | 0.69 | 0.73 | 1.09 | 0.65 |
| | 25 | 0.92 | 0.70 | 0.43 | 1.25 | 0.88 | 1.02 | 0.79 |
| | 10 | 1.01 | 1.10 | 1.76 | 1.60 | 1.37 | 1.14 | 1.02 |

| | μg/ml | U373 | A549 | PC3 | THP1 | MCF7 | SKOV3 | CCD1079SK |
|---|---|---|---|---|---|---|---|---|
| Toxicity (error) | 100 | 0.05 | 0.04 | 0.00 | 0.02 | 0.05 | 0.04 | 0.07 |
| | 75 | 0.06 | 0.04 | 0.00 | 0.06 | 0.02 | 0.01 | 0.03 |
| | 50 | 0.03 | 0.03 | 0.01 | 0.01 | 0.04 | 0.13 | 0.08 |

TABLE 4-continued

| | | \u00b5g/ml | | | | | | |
|---|---|---|---|---|---|---|---|---|
| | | 25 | 0.01 | 0.03 | 0.05 | 0.06 | 0.12 | 0.07 | 0.06 |
| | | 10 | 0.05 | 0.10 | 0.16 | 0.07 | 0.03 | 0.04 | 0.01 |

Multiplex evaluation of CC primary extract #1

| | µg/ml | U373 | A549 | PC3 | THP1 | MCF7 | SKOV3 | CCD1079SK |
|---|---|---|---|---|---|---|---|---|
| Ratio | 100 | *5.00* | *4.89* | *2.31* | *2.40* | *2.62* | *3.35* | *2.17* |
| | 75 | *4.54* | *4.72* | *2.49* | *3.16* | *2.16* | *3.95* | *2.08* |
| | 50 | *3.70* | *4.78* | *2.62* | *3.58* | *2.09* | *3.66* | *1.91* |
| | 25 | *3.34* | *4.13* | *3.37* | *3.46* | *1.76* | *2.99* | *2.25* |
| | 10 | *1.91* | *1.53* | *1.93* | *1.81* | *1.49* | *2.00* | *1.17* |

Example 4. Fractionation and Analysis

C.C. crude extract #1 (0.2 g) was initially fractionated into 5 fractions by C-18 SPE column separation using 15 ml each of 5% MeOH (fraction 1-1), 25% MeOH (fraction 1-2), 50% MeOH (fraction 1-3), MeOH (fraction 1-4) and MeOH:$CH_2Cl_2$ (1:1) (fraction 1-5). The amounts obtained from this strategy are summarized in Table 5.

TABLE 5

| Fractions | Yield (mg) |
|---|---|
| 1-1 | 147.05 |
| 1-2 | 3.88 |
| 1-3 | 2.35 |
| 1-4 | 19.81 |
| 1-5 | 2.90 |

CIMA Evaluation of Fractions from Extract 1:

Cells were seeded in 96 well plates and incubated with the indicated concentration of fractions (1-1, 1-2, 1-3, 1-4 or 1-5) for 72 h prior to CIMA assay. Equivalent concentrations of DMSO vehicle alone served as controls for each test concentration. Mean absorbance values from quadruplicate wells were expressed as percent changes relative to DMSO vehicle. Decreases exceeding 25% relative to controls were considered significant (Bold). Where sufficient inhibition of cell viability/proliferation was observed to support analysis, 50% inhibitory concentrations ($IC_{50}$) are indicated in µg/ml. As shown in Table 6, Activity was predominantly observed in fraction 4.

TABLE 6

Evaluation by CIMA of fractions 1 to 5 from C.C. extract #1

1.1

| µg/ml | U373 | A549 | PC3 | THP1 | MCF7 | SKOV3 |
|---|---|---|---|---|---|---|
| 100 | −15.63 | 15.86 | −16.57 | −28.62 | 10.60 | 17.68 |
| 75 | −14.01 | 4.29 | −10.70 | −16.65 | 14.15 | 17.06 |
| 50 | −19.94 | 6.31 | −12.79 | −17.95 | 6.32 | 17.91 |
| 25 | −17.33 | −0.51 | −10.25 | −14.28 | −0.41 | 12.18 |
| 10 | −13.86 | −0.72 | −10.34 | −8.48 | −1.31 | 12.93 |
| 5 | −11.58 | −4.74 | −12.92 | −4.01 | 0.10 | 9.38 |
| 2.5 | −11.31 | 0.32 | −6.88 | −6.31 | 7.93 | 20.38 |
| 0 | 0.00 | 0.00 | 0.00 | 0.00 | 0.00 | 0.00 |
| IC50 | — | — | — | — | — | — |

1.2

| µg/ml | U373 | A549 | PC3 | THP1 | MCF7 | SKOV3 |
|---|---|---|---|---|---|---|
| 100 | −30.49 | −22.16 | −29.95 | −24.91 | 2.26 | 10.43 |
| 75 | −28.49 | 0.20 | −24.38 | −25.29 | 1.51 | 13.75 |
| 50 | −32.12 | −1.12 | −23.21 | −24.15 | 1.48 | 7.69 |
| 25 | −26.60 | 2.25 | −14.97 | −25.43 | −2.75 | 8.18 |
| 10 | −26.10 | −2.28 | −17.96 | −20.18 | −11.99 | 9.33 |
| 5 | −26.68 | −3.92 | −20.18 | −8.53 | −11.57 | 2.46 |
| 2.5 | −22.19 | −5.19 | −13.07 | −3.02 | −10.33 | 3.77 |
| 0 | 0.00 | 0.00 | 0.00 | 0.00 | 0.00 | 0.00 |
| IC50 | — | — | — | — | — | — |

1.3

| µg/ml | U373 | A549 | PC3 | THP1 | MCF7 | SKOV3 |
|---|---|---|---|---|---|---|
| 100 | −28.52 | 4.04 | −23.64 | −35.63 | 6.44 | −3.56 |
| 75 | −29.00 | 14.38 | −11.02 | −36.79 | 17.77 | 7.29 |
| 50 | −25.00 | 18.32 | −10.35 | −22.20 | 9.42 | 9.96 |
| 25 | −22.74 | 12.73 | −10.67 | −22.01 | 4.17 | 13.50 |
| 10 | −20.53 | 13.66 | −5.54 | −20.21 | 2.84 | 14.03 |
| 5 | −15.43 | 14.78 | −12.43 | −6.77 | −0.33 | 7.24 |
| 2.5 | −14.77 | 19.96 | −9.10 | −2.01 | 0.83 | 14.70 |
| 0 | 0.00 | 0.00 | 0.00 | 0.00 | 0.00 | 0.00 |
| IC50 | — | — | — | — | — | — |

1.4

| µg/ml | U373 | A549 | PC3 | THP1 | MCF7 | SKOV3 |
|---|---|---|---|---|---|---|
| 100 | −69.37 | −57.58 | −81.67 | −61.26 | −41.01 | −41.95 |
| 75 | −54.05 | −55.82 | −77.91 | −43.80 | −16.76 | |
| 50 | −58.02 | −52.65 | −67.85 | −30.37 | −14.88 | −24.52 |
| 25 | −45.72 | −29.57 | −27.95 | −21.24 | −10.80 | 13.04 |
| 10 | −20.40 | −6.90 | −20.75 | −14.23 | −11.76 | 15.02 |
| 5 | −18.34 | 1.63 | −17.44 | −8.55 | −9.77 | 9.97 |
| 2.5 | −16.41 | 13.03 | −14.87 | −5.01 | −0.59 | 14.81 |
| 0 | 0.00 | 0.00 | 0.00 | 0.00 | 0.00 | 0.00 |
| IC50 | 33.75 | 47.25 | 39.00 | 83.75 | — | — |

1.5

| µg/ml | U373 | A549 | PC3 | THP1 | MCF7 | SKOV3 |
|---|---|---|---|---|---|---|
| 100 | −30.55 | −29.65 | −35.43 | −37.72 | 4.07 | 19.18 |
| 75 | −20.36 | −8.67 | −19.20 | −28.59 | 18.15 | 14.54 |
| 50 | −21.41 | −3.69 | −18.94 | −28.91 | 13.12 | 6.01 |
| 25 | −16.99 | 1.94 | −10.54 | −24.49 | 16.03 | 5.10 |
| 10 | −15.88 | 15.48 | −14.09 | −20.89 | 8.17 | 11.85 |
| 5 | −16.18 | 15.26 | −17.04 | −4.65 | 3.36 | 6.92 |
| 2.5 | −16.66 | 31.29 | −11.66 | 0.11 | 6.73 | 16.16 |
| 0 | 0.00 | 0.00 | 0.00 | 0.00 | 0.00 | 0.00 |
| IC50 | — | — | — | — | — | — |

Example 5. Analytical Profiling

Figure 5:
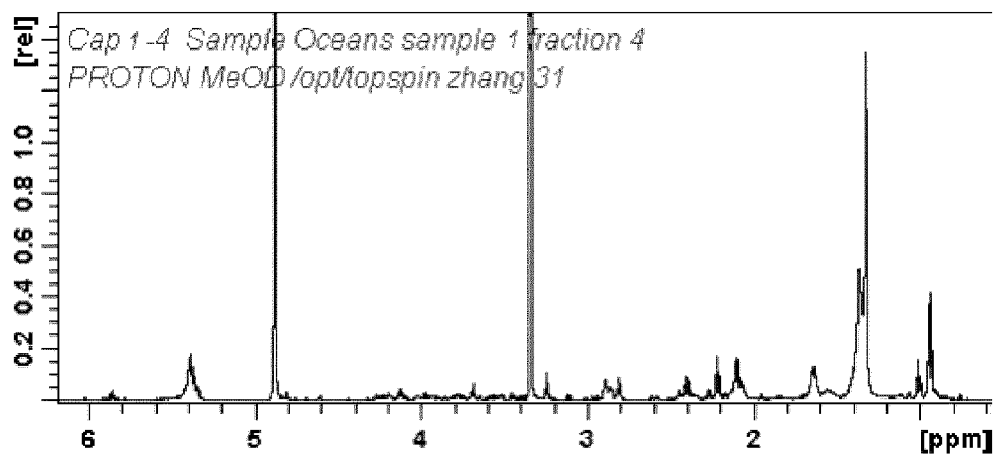
FIG. 5. Proton-NMR profiling of fraction 1-4 from CC.

In the anti-cancer analysis, fraction 1-4 exhibited strong activity (Table 6). This fraction was subjected to NMR analysis in order to provide insight into its composition as shown in FIG. 5.

For NMR analysis, samples were dissolved in either MeOH-$d_6$ and then transferred to 1.7 mm NMR tube. $^1$H-NMR spectra were acquired on a Bruker Avance III 600

MHz NMR spectrometer operating at 600.283 MHz $^1$H observation frequency and a temperature of 25±0.1° C.

For LC-MS analysis (not shown), separation was conducted on an Agilent Zorbax Eclipse XDB-C18 (2.1×100 mm, 3.5 µm) column using an HPLC 1100 MSD system. Solvent A was water with 0.1% formic acid and solvent B was acetonitrile with 0.1% formic acid. A gradient from 50% to 100% solution B was used at flow rate of 0.3 ml/min. Mass spectra were obtained on an Agilent MSD system using the following conditions: drying gas flow (L/min): 10; nebulizer pressure (psig): 30; drying gas temperature (° C.): 350; capillary voltage (V): 4000 (positive) and 3500 (negative).

Evaluation of the four dominant peaks in the spectrum for fraction 1-4 (FIG. 5) revealed the presence of —CH═CH— (about 5.4) and —CH$_2$—CH$_2$— (about 2.8-2.9 and about 2.0-2.3) chains indicative of predominantly unsaturated fatty acid species. This observation was further confirmed following LC-MS analysis of fraction 1-4 (not shown).

Example 6. Seasonal Study for *Chaetomorpha Cannabina* Anti-Cancer Activity

Seasonal study for *Chaetomorpha Cannabina* anti-cancer activity was established for different geographical regions—2 sites on the west coast and south coast of Newfoundland and Labrador, and over 2 time periods—July and September.

6. 1 Experimental
  Compound Preparation:
  Stock solutions of the extracts were prepared in dimethylsulfoxide (DMSO) at 10 mg/ml and stored in 200 µl aliquots at −20° C. until use. This preparation ensured that the DMSO content delivered to cells in culture never exceeded 1%.
  CIMA Assay:
  The effects of test extracts were assessed following chronic exposure conditions in which cells were seeded at 2×10$^3$ cells/well (96 well plate) and incubated with test compounds for 72 h. Each compound was evaluated over a range of concentrations (0, 10, 25, 50, 75 or 100 µg/ml). Cell proliferation was initially assessed using a standard colorimetric indicator of metabolic activity (CIMA) assay. In this assay, tetrazole reduction was evaluated as a measure of metabolic function that evaluates mitochondrial activity to determine the extent of cell proliferation within a culture. This assay is based on the reduction of yellow tetrazolium salt to purple formazan by mitochondrial reductases enzymes in viable cells, resulting in a colour change that confers a change in absorbance (λ=500-600 nm). Six human cell lines were selected for evaluation: U373 (glioblastoma-astrocytoma), A549 (lung carcinoma), THP1 (acute monocytic leukemia), MCF7 (mammary gland adenocarcinoma), SKOV3 (ovarian adenocarcinoma) and CCD1079SK (fibroblast, noncancerous but proliferating). A multiplex cytotoxicity assay was used following the CIMA assay to further elucidate the actions of select fractions.

6.2. Results
  Anti-cancer: Four (4) extracts from Table 1 were tested for anti-cancer activity by CIMA analysis. Results are summarized in Table 7 for all cells as fold changes relative to vehicle controls with changes >25% identified in red. All extracts exhibited activity in the assay, although in general, U373 and SKOV3 cells were resistant to reduced viability. Prioritizing hits on the basis of dose-dependency, intensity and activity across multiple cell types yields, extract #6 was selected for follow-up multiplex analysis and yielded a profile consistent with decreased viability in the absence of overt cytotoxicity, suggesting an anti-proliferative effect. Extract #3 was therefore selected for further in vivo testing against a breast cancer cell line.

TABLE 7

Summary of CIMA Results

| SAMPLE | µg/ml | CCD | MCF-7 | THP-1 | A549 | U373 | SKOV3 |
|---|---|---|---|---|---|---|---|
| 2 | 10 | 0.939 | 0.978 | 1.019 | 1.067 | 1.111 | 1.060 |
|  | 25 | 0.772 | 0.879 | 0.955 | 0.933 | 0.982 | 1.079 |
|  | 50 | 0.800 | 0.822 | 1.002 | 0.851 | 1.000 | 1.093 |
|  | 75 | 0.806 | 0.726 | 1.008 | 0.800 | 0.942 | 0.968 |
|  | 100 | 0.731 | 0.649 | 1.013 | 0.777 | 0.923 | 0.907 |
| 3 | 10 | 0.650 | 0.746 | 0.813 | 0.812 | 0.953 | 1.142 |
|  | 25 | 0.503 | 0.720 | 0.850 | 0.778 | 0.894 | 1.082 |
|  | 50 | 0.601 | 0.637 | 0.770 | 0.861 | 0.958 | 1.096 |
|  | 75 | 0.515 | 0.516 | 0.715 | 0.627 | 0.956 | 0.954 |
|  | 100 | 0.509 | 0.440 | 0.648 | 0.606 | 0.840 | 0.930 |
| 4 | 10 | 0.654 | 0.812 | 0.676 | 0.905 | 0.989 | 1.040 |
|  | 25 | 0.728 | 0.783 | 0.896 | 0.896 | 0.975 | 1.021 |
|  | 50 | 0.726 | 0.782 | 0.933 | 0.862 | 0.946 | 1.084 |
|  | 75 | 0.708 | 0.710 | 0.870 | 0.826 | 0.888 | 0.902 |
|  | 100 | 0.690 | 0.716 | 0.811 | 0.736 | 0.902 | 0.963 |
| 5 | 10 | 0.553 | 0.701 | 0.830 | 0.791 | 0.950 | 1.137 |
|  | 25 | 0.687 | 0.614 | 0.955 | 0.781 | 1.114 | 0.952 |
|  | 50 | 0.584 | 0.637 | 0.907 | 0.751 | 0.944 | 1.041 |
|  | 75 | 0.587 | 0.546 | 0.960 | 0.771 | 0.875 | 0.888 |
|  | 100 | 0.642 | 0.600 | 1.005 | 0.680 | 0.901 | 0.921 |

Example 7. Evaluation of *Chaetomorpha Cannabina* (CC) Crude Extract #3 in a Murine Flank Tumor Model C.C. crude extract #3 (see Table 1) was found to be anti-proliferative in vivo, at both 10 and 25 mg/kg, as evidenced by the failure of tumour volumes to increase over the 6-week treatment regimen. This effect occurred in the absence of overt adverse effects, defined as detrimental changes in body weights or physical distress in treatment groups that would have necessitated termination of the study. Animals treated with extract #3 did present mild neurological symptoms (hyperactivity and hyperreactivity) that were dose-dependent. However, the severity of these symptoms remained stable throughout the trial and did not approach clinical levels that were considered adverse.

7.1 Quantified Technical Objective
  To evaluate the efficacy of a *Chaetomorpha Cannabina* crude extract (#3) in a nude mouse flank tumour model over a 6-week treatment regimen.

Figure 6:
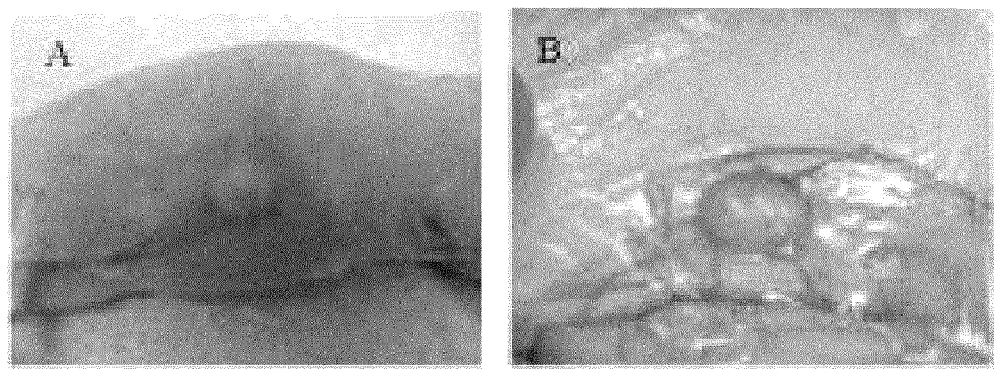
FIG. 6. Representative images of tumour xenografts demonstrating external (A) and subcutaneous (B) profiles. The extent of angiogenesis is shown in the network of blood vessels in panel B.

7.2 Work Plan:
  Establishing the tumour model: Animal studies were conducted under ACC protocol #14-007 approved by the Atlantic Veterinary College (AVC, PEI). Briefly, homozygous outbred nude mice (strain J:NU, 6-weeks old, female) suitable as immunodeficient tumour transplant hosts were procured from a commercial supplier (Jackson Labs, Maine) and acclimatized in a barrier facility (AVC) for one week. Mice were weighed and random groups of eight to ten mice were established as follows:
  Group 1: C.C. crude extract #3 (NC-62), 10 mg/kg
  Group 2: C.C. crude extract #3, (NC-62), 25 mg/kg
  Group 5: No treatment control
  Group 6: Vehicle control (VC, DMSO, <1% v/v)
  To establish the tumours, MDA-MB-231 breast cancer cells (2×10$^7$ cells/100 µl 50:50 matrigel:DMEM) were injected subcutaneously into both right and left flanks. Tumours were evaluated over a 2 week period until sufficient volume (growth to approximately 20 mm³) for subsequent analysis occurred. During this period, body weights were measured twice weekly. Representative figures demonstrating tumour positioning and features (size, extent of angiogenesis, etc.) are shown in FIG. 6.

Evaluation of Seaweed Extract:

Mice in which tumours had been established were treated every second day by intraperitoneal injections of C.C. crude extract #3 (NC-62) test extract over a 6-week time course. From each group a minimum of 12 tumours were selected for analysis. Tumours were measured weekly using external calipers and volumes established using the modified ellipsoidal formula: tumour volume=0.5 (length×width²)

7.3 Results

Figure 7:
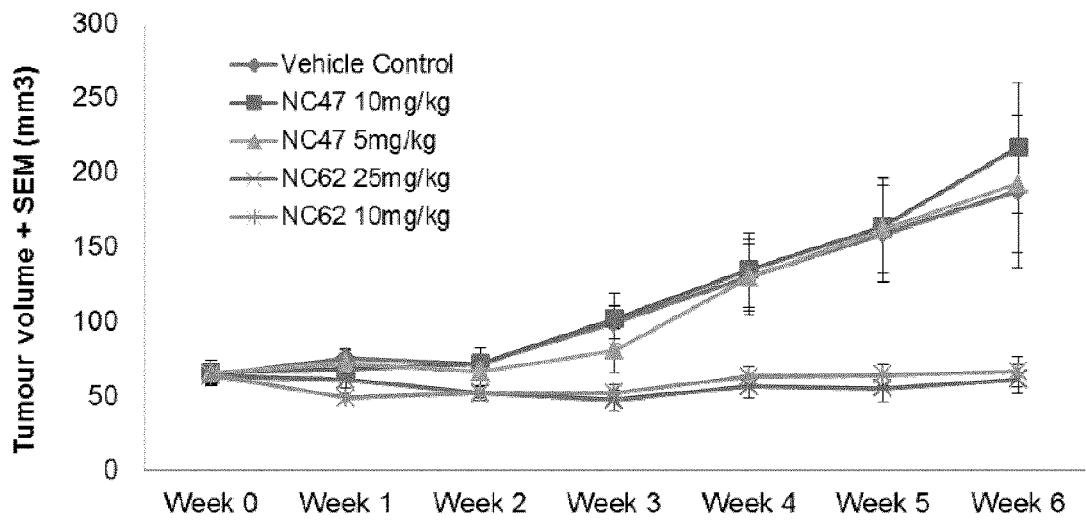
FIG. 7. Tumor volumes over the six-week time course of treatment with extract #1-4 from CC.

Tumour Volumes:

Over the course of the study, tumour volumes in control groups increased by approximately 3-fold, from 65 mm³ to 190 mm³ (Table 8, FIG. 7). No significant change in tumour size was observed in mice treated with extract #3 at either 10 or 25 mg/kg during the 6-week study. On average, tumours in C.C. #3-treated groups remained at the 65 mm³ starting volume. This profile of tumours failing to progress in size suggest that C.C. extract #3 exerted an anti-proliferative effect.

TABLE 9

Specimen data

| Specimen # | Date Collected | Location | Yields |
|---|---|---|---|
| Chaetomorpha Cannabina (77) | July 2013 | Rocky Harbour, NF | 8.00% |

8.2 Experimental Design

Extracts preparation: Stock solutions of the extract were prepared in dimethylsulfoxide (DMSO) at 10 mg/ml and stored in 200 µl aliquots at −20° C. until used. Working concentrations were prepared by direct dilution of the stock solution into complete culture medium. This preparation ensured that the DMSO content delivered to cells in culture never exceeded 1%.

8.3 Cell Proliferation Assay

The effects of the extracts were assessed following chronic exposure conditions in which cells were seeded at 2×10³ cells/well and incubated with test compounds for 72 h. Each extract was evaluated over a range of concentrations (0, 1, 10, 25, 50, or 100 µg/ml) and 50% inhibitory concentrations ($IC_{50}$) established as warranted. Cell proliferation was assessed using a standard colorimetric indicator of metabolic activity (CIMA) assay. In this assay, tetrazole reduction was assessed as a measure of metabolic function by quantifying mitochondrial activity as a measure of the

TABLE 8

Tumour volume over the six-week time course

| Group | Concentration (mg/kg) | # tumors | Tumor Volume (mm³) ± SEM | | | | | | | ANOVA (P value) |
|---|---|---|---|---|---|---|---|---|---|---|
| | | | Week 0 | Week 1 | Week 2 | Week 3 | Week 4 | Week 5 | Week 6 | |
| Vehicle control | — | N = 14 | 64 ± 5 | 75 ± 7 | 71 ± 6 | 99 ± 11 | 130 ± 23 | 159 ± 32 | 187 ± 51 | 0.007 |
| C.C extract #3 | 25 | N = 12 | 63 ± 6 | 61 ± 5 | 52 ± 5* | 47 ± 7¶ | 56 ± 7* | 55 ± 8¶ | 61 ± 10* | 0.708 |
| | 10 | N = 16 | 72 ± 7 | 55 ± 5¶ | 61 ± 7* | 82 ± 20¶ | 63 ± 7* | 67 ± 8* | 67 ± 10* | 0.224 |

ANOVA, variance in tumour volume by week within each group; P > 0.05 indicates no change over time (F > $F_{crit}$)
¶Student's t-test vs vehicle control at each week, P < 0.01
*Student's t-test vs vehicle control at each week, P < 0.05

Figure 8:
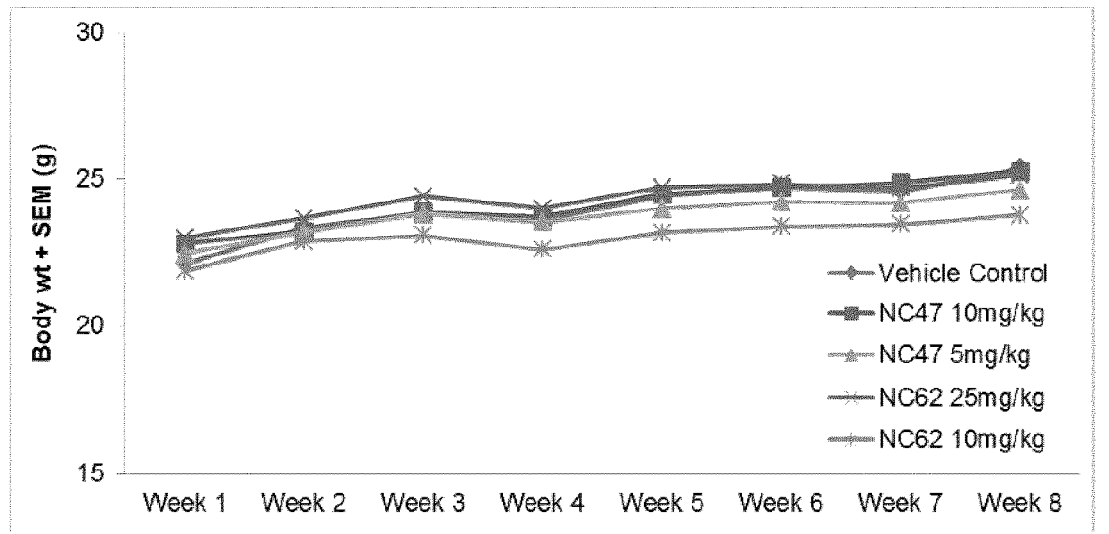
FIG. 8. Body weights over the eight week study duration.

Body Weights:

Over the study course, the body weights of mice in all treatment groups remained stable with no adverse effects observed (FIG. 8). The average starting weight was 22 g and average weight at study end was 25 g.

Conclusion:

The study results are promising and suggestive of potential in vivo anti-proliferative activity of cancer cells with extract #3 from Chaetomorpha Cannabina.

Example 8—Further Anti-Cancer Screening of Chaetomorpha Cannabina Extracts 8.1 New Specimen Further specimens of Chaetomorpha Cannabina were collected during 2013 (Table 9). Extraction was performed as detailed in Example 1 (80% aqueous ethanol). C.C. crude extracts #77 was further used for confirmatory anti-cancer screening.

extent of cell proliferation within a culture. This assay is based on the reduction of yellow tetrazolium salt to purple formazan by mitochondrial reductases enzymes in viable cells, resulting in a colour change that confers a change in absorbance. This change was quantified using a spectrophotometer ($\lambda$=500-600 nm). Samples were diluted as required to ensure that values obtained with the MTT assay fell within the linear range of the protocol. Qualitative microscopic evaluation of treated cultures was used to supplement the quantitative CIMA data. Seven cell lines were employed in this study: CCD1079SK (primary human fibroblasts), PC3 (prostate cancer), SK-OV-3 (ovarian adenocarcinoma), MCF-7 (mammary gland adenocarcinoma), U373 (glioblastoma-astrocytoma), THP-1 (acute monocytic leukemia), and A549 (lung carcinoma).

8.4 Results

The results of the anti-cancer analysis are summarized in Table 10 as percent viability (mean+standard deviation of four replicates). Decreased activity greater than 25% (in bold) was considered significant.

TABLE 10

Evaluation of anti-cancer activity for CC extract #77

| Conc. | A549 | | PC3 | | MCF7 | | SKOV3 | |
|---|---|---|---|---|---|---|---|---|
| μg/ml | AVG | SD | AVG | SD | AVG | SD | AVG | SD |
| 1 | 94.6 | 4.6 | 98.2 | 1.3 | 101.8 | 12.8 | 95.5 | 5.7 |
| 10 | 81.7 | 2.7 | 91.7 | 2.0 | 78.7 | 3.9 | 84.7 | 4.0 |
| 25 | 78.8 | 3.1 | 86.4 | 3.4 | 72.7 | 3.6 | 79.8 | 4.8 |
| 50 | 77.1 | 2.4 | 77.2 | 4.0 | 60.3 | 2.6 | 72.3 | 3.7 |
| 100 | 67.5 | 1.6 | 82.5 | 2.2 | 45.6 | 1.0 | 50.9 | 4.6 |

| Conc. | U373 | | THP-1 | | CCD-1079-SK | | |
|---|---|---|---|---|---|---|---|
| μg/ml | AVG | SD | AVG | SD | AVG | SD | IC$_{50}$ μg/ml |
| 1 | 94.6 | 2.7 | 99.4 | 7.2 | 100.3 | 10.3 | MCF7: 81.9 |
| 10 | 61.8 | 4.6 | 88.2 | 3.7 | 82.2 | 7.6 | U373: 66.1 |
| 25 | 57.0 | 2.8 | 67.9 | 4.4 | 67.3 | 3.6 | THP-1: 75.9 |
| 50 | 55.7 | 3.0 | 52.2 | 1.7 | 65.5 | 4.5 | |
| 100 | 48.4 | 2.0 | 40.8 | 1.2 | 60.3 | 4.6 | |

1. Bold text indicates decreased activity exceeding 25% of matched control values

Example 9—Fractionation and Secondary Screening of *Chaetomorpha Cannabina* (CC) Extract #77

To evaluate CC extract and select fractions for biological activity in anti-cancer assay, the following was undertaken:
1) Conduct secondary bio-assay screening to confirm activity of CC extract;
2) Fractionate CC extract and evaluate these fractions in biological assays;
3) Acquire information on the group of chemicals responsible for bioactivity and identify bioactive markers for standardization of extract and product formulation.

9.1 Experimental Design

Extract Preparation:

Stock solutions of the extract was prepared in dimethyl-sulfoxide (DMSO) at 10 mg/ml and stored in 200 μl aliquots at −20° C. until use. This preparation ensured that the DMSO content delivered to cells in culture never exceeded 1%.

CIMA Assay:

The effects of test extract was assessed following chronic exposure conditions in which cells were seeded at 2×10$^3$ cells/well (96 well plate) and incubated with test compounds for 72 h. Each fraction was evaluated over a range of six concentrations (0, 1, 10, 25, 50, or 100 μg/ml) where sufficient material was available and 50% lethal doses (LD$_{50}$) established if warranted. Cell proliferation was initially assessed using a standard colorimetric indicator of metabolic activity (CIMA) assay. In this assay, tetrazole reduction was evaluated as a measure of metabolic function that evaluates mitochondrial activity to determine the extent of cell proliferation within a culture. This assay is based on the reduction of yellow tetrazolium salt to purple formazan by mitochondrial reductases enzymes in viable cells, resulting in a colour change that confers a change in absorbance ($\lambda$=500-600 nm). Five human cell lines were selected for evaluation: U373 (glioblastoma-astrocytoma), THP1 (acute monocytic leukemia), MCF7 (mammary gland adenocarcinoma), SKOV3 (ovarian adenocarcinoma) and CCD1079SK (primary human fibroblasts) cells.

Fractionation Strategy:

Crude CC extracts were fractionated as detailed in the diagram from FIG. 2. Briefly, primary extracts were initially fractionated into 5 fractions by C-18 column separation.

9.2 Fractionation and Analysis.

CC crude extract #77 (0.5 g) was initially fractionated into 5 fractions by C-18 SPE column separation using 15 ml each of 5% MeOH (fraction 1), 25% MeOH (fraction 2), 50% MeOH (fraction 3), MeOH (fraction 4) and MeOH:CH$_2$Cl$_2$ (1:1) (fraction 5). The amounts obtained from this strategy are summarized in Table 11.

TABLE 11

CC 77 (2.04 g)

| Fractions | Yield (mg) |
|---|---|
| F77.1 | 1.439 |
| F77.2 | 0.156 |
| F77.3 | 0.076 |
| F77.4 | 0.212 |
| F77.5 | 0.191 |

9.3 Results

CIMA Evaluation of Primary Extract

C.C. crude extracts #77 exhibited high activity and LD$_{50}$ values that could be calculated. This data is summarized in Table 12.

Evaluation of CC Primary Extract by CIMA

Cells were seeded in 96 well plates and incubated with the indicated concentration of CC primary extract for 72 h prior to CIMA assay. Equivalent concentrations of DMSO vehicle alone served as controls for each test concentration. Mean absorbance values from triplicate wells were expressed as percent changes relative to DMSO vehicle. Values are expressed as percent viability+standard deviation. Decreases exceeding 25% relative to controls were considered significant (red). Where sufficient inhibition of cell viability/proliferation was observed to support analysis, 50% lethal doses (LD$_{50}$) are indicated in μg/ml. Several CC fractions were significantly active across a broad range of cell types. Particularly, fractions 4 and 5 were active against several cancer cell types, more particularly fractions F77.4.

TABLE 12

Evaluation by CIMA of fractions 1 to 5 from C.C. crude extract #77
*Chaetomorpha Cannabina* (77)

| | Conc. (μg/ml) | SKOV3 | | MCF7 | | U373 | | THP-1 | | CCD1079SK | |
|---|---|---|---|---|---|---|---|---|---|---|---|
| | | AVG | SD | AVG | SD | AVG | SD | AVG | SD | AVG | SD |
| F1 | 1 | 103.6 | 8.2 | 103.3 | 6.4 | 103.1 | 12.3 | 75.7 | 1.8 | 102.7 | 4.4 |
| | 10 | 101.0 | 11.1 | 103.4 | 2.2 | 103.9 | 6.3 | 75.9 | 3.7 | 100.7 | 5.1 |
| | 25 | 100.0 | 6.3 | 105.8 | 6.4 | 85.4 | 9.2 | 74.5 | 3.1 | 99.3 | 1.5 |
| | 50 | 104.2 | 12.5 | 98.4 | 4.9 | 85.3 | 8.4 | 79.5 | 3.2 | 102.4 | 8.2 |
| | 100 | 92.4 | 8.9 | 92.6 | 11.2 | 81.1 | 3.6 | 68.1 | 0.9 | 91.9 | 4.5 |
| | LD$_{50}$ | — | | — | | — | | — | | 33.1 | |

TABLE 12-continued

Evaluation by CIMA of fractions 1 to 5 from C.C. crude extract #77
*Chaetomorpha Cannabina* (77)

| | Conc. (µg/ml) | SKOV3 AVG | SD | MCF7 AVG | SD | U373 AVG | SD | THP-1 AVG | SD | CCD1079SK AVG | SD |
|---|---|---|---|---|---|---|---|---|---|---|---|
| F2 | 1 | 102.3 | 5.3 | 101.1 | 3.6 | 101.6 | 8.2 | 80.4 | 3.5 | 98.3 | 9.8 |
| | 10 | 99.5 | 3.9 | 106.8 | 5.4 | 103.2 | 10.1 | 78.9 | 5.1 | 99.5 | 13.5 |
| | 25 | 94.0 | 0.6 | 100.0 | 2.8 | 92.1 | 7.9 | 80.0 | 4.9 | 101.8 | 11.5 |
| | 50 | 92.6 | 3.5 | 99.4 | 7.3 | 82.3 | 5.9 | 78.2 | 8.4 | 103.0 | 12.1 |
| | 100 | 91.4 | 2.3 | 98.8 | 4.4 | 69.0 | 6.3 | 70.8 | 4.1 | 93.3 | 8.8 |
| | $LD_{50}$ | — | | — | | — | | — | | 93.3 | |
| F3 | 1 | 100.9 | 12.3 | 105.7 | 4.7 | 97.8 | 6.2 | 82.7 | 5.9 | 97.3 | 10.9 |
| | 10 | 91.4 | 10.9 | 101.1 | 4.2 | 102.2 | 8.1 | 75.0 | 3.1 | 93.8 | 8.1 |
| | 25 | 87.5 | 9.7 | 92.9 | 8.2 | 102.6 | 9.2 | 75.6 | 5.0 | 85.8 | 13.8 |
| | 50 | 77.0 | 11.0 | 52.5 | 6.2 | 83.0 | 5.8 | 75.5 | 4.1 | 85.6 | 8.6 |
| | 100 | 51.3 | 7.0 | 27.8 | 2.5 | 49.2 | 3.1 | 54.3 | 1.7 | 60.6 | 8.4 |
| | $LD_{50}$ | — | | — | | — | | — | | — | |
| F4 | 1 | 95.0 | 2.5 | 97.1 | 11.3 | 103.2 | 14.9 | 87.0 | 7.8 | 89.2 | 4.7 |
| | 10 | 68.3* | 4.7 | 80.4 | 15.2 | 93.6 | 7.0 | 81.3 | 3.2 | 84.0 | 1.5 |
| | 25 | 60.7* | 6.2 | 73.3* | 7.9 | 93.4 | 6.9 | 79.1 | 5.8 | 81.2 | 3.4 |
| | 50 | 53.8# | 3.4 | 50.3* | 3.0 | 87.2 | 5.4 | 78.8 | 4.1 | 76.8 | 6.0 |
| | 100 | 50.1* | 5.8 | 43.2# | 5.4 | 60.7 | 4.2 | 74.9 | 3.7 | 68.1 | 6.7 |
| | $LD_{50}$ | — | | — | | — | | — | | — | |
| F5 | 1 | 108.4 | 9.9 | 98.9 | 2.9 | 117.7 | 7.4 | 93.9 | 5.6 | 98.5 | 1.9 |
| | 10 | 93.9 | 12.9 | 96.0 | 3.7 | 106.0 | 2.6 | 93.2 | 7.5 | 96.9 | 5.1 |
| | 25 | 95.1 | 12.1 | 96.7 | 7.5 | 90.3 | 2.0 | 92.4 | 8.6 | 98.8 | 6.2 |
| | 50 | 96.3 | 4.3 | 91.1 | 2.9 | 84.4 | 3.1 | 99.1 | 10.9 | 100.1 | 4.5 |
| | 100 | 100.8 | 10.8 | 82.3 | 2.5 | 72.2 | 1.9 | 98.8 | 9.5 | 96.6 | 4.1 |
| | $LD_{50}$ | — | | — | | — | | — | | — | |

1. Bold text indicates decreased activity exceeding 25% of matched control values
2. #$p < 0.001$, *$p < 0.01$, ≠$p < 0.05$
3. —, $LD_{50} > 100$ µg/ml

Example 10—Primary Anti-Cancer Screening of *Cladophora Sericea* (C.S.) Extract

10.1 Extraction and Yields

C.S. extraction was performed as detailed in Example 1 (80% aqueous ethanol). Yields were calculated for the extract of *Cladophora Sericea* collected during Fall 2014. Yield was 4.95 when expressed as g of dry extract per kg of fresh seaweed, and 42.3, when expressed as g of dry extract per kg of dry seaweed (Table 13). 30 mg of the extract was used for anti-cancer screening.

TABLE 13

Extraction Yields

| Specimen | Date Collected | Location | Extract dry weight (g) C | Yield C/A[a] g of dry extract/ kg of wet plant | Yield C/B[b] g of dry extract/ kg of dry plant |
|---|---|---|---|---|---|
| *Cladophora Sericea* | Sep. 6, 2014 | Pinware, NF | 1.1 | 4.95 | 42.3 |

10.2 Experimental Design

Extracts Preparation:

Stock solutions of the extract was prepared in dimethyl-sulfoxide (DMSO) at 10 mg/ml and stored in 200 µl aliquots at −20° C. until used. Working concentrations were prepared by direct dilution of the stock solution into complete culture medium. This preparation ensured that the DMSO content delivered to cells in culture never exceeded 1%.

10.3 Cell Proliferation Assay

The effects of the extracts were assessed following chronic exposure conditions in which cells were seeded at $2 \times 10^3$ cells/well and incubated with test compounds for 72 h. Each extract was evaluated over a range of concentrations (0, 1, 10, 25, 50, or 100 µg/ml) and 50% inhibitory concentrations ($IC_{50}$) established as warranted. Cell proliferation was assessed using a standard colorimetric indicator of metabolic activity (CIMA) assay. In this assay, tetrazole reduction was assessed as a measure of metabolic function by quantifying mitochondrial activity as a measure of the extent of cell proliferation within a culture. This assay is based on the reduction of yellow tetrazolium salt to purple formazan by mitochondrial reductases enzymes in viable cells, resulting in a colour change that confers a change in absorbance. This change was quantified using a spectrophotometer ($\lambda = 500$-$600$ nm). Samples were diluted as required to ensure that values obtained with the MTT assay fell within the linear range of the protocol. Qualitative microscopic evaluation of treated cultures was used to supplement the quantitative CIMA data. Seven cell lines were employed in this study: CCD1079SK (primary human fibroblasts), PC3 (prostate cancer), SK-OV-3 (ovarian adenocarcinoma), MCF-7 (mammary gland adenocarcinoma), U373 (glioblastoma-astrocytoma), THP-1 (acute monocytic leukemia), and A549 (lung carcinoma).

10.4 Results

The results of the anti-cancer analysis are summarized in Table 14 as percent viability (mean+standard deviation of four replicates). Decreased activity greater than 25% (in bold) was considered significant.

TABLE 14

Evaluation of anti-cancer activity for C.S. crude extract

| Conc. (µg/ml) | A549 AVG | A549 SD | PC3 AVG | PC3 SD | MCF7 AVG | MCF7 SD | SKOV3 AVG | SKOV3 SD |
|---|---|---|---|---|---|---|---|---|
| 1 | 101.4 | 3.1 | 99.8 | 9.2 | 98.8 | 8.0 | 90.0 | 2.7 |
| 10 | 96.9 | 2.8 | 114.6 | 8.4 | 92.9 | 4.3 | 90.8 | 5.3 |
| 25 | 95.3 | 4.3 | 116.0 | 13.0 | 77.5 | 6.7 | 86.2 | 4.7 |
| 50 | 89.9 | 4.5 | 106.6 | 8.4 | 48.7 | 3.1 | 67.5 | 3.4 |
| 100 | 62.8 | 5.4 | 94.8 | 7.8 | 37.9 | 4.8 | 48.3 | 1.2 |

| Conc. (µg/ml) | U373 AVG | U373 SD | THP-1 AVG | THP-1 SD | CCD-1079-SK AVG | CCD-1079-SK SD | IC$_{50}$ (µg/ml) |
|---|---|---|---|---|---|---|---|
| 1 | 86.6 | 3.1 | 92.7 | 7.8 | 92.2 | 5.6 | MCF7: 70.2 |
| 10 | 89.2 | 4.6 | 65.4 | 4.7 | 89.3 | 6.4 | SKOV3: 95.2 |
| 25 | 79.0 | 3.4 | 54.9 | 1.4 | 77.1 | 6.5 | U373: 90.3 |
| 50 | 73.0 | 2.7 | 56.0 | 1.1 | 71.2 | 2.7 | THP-1: 42.8 |
| 100 | 43.1 | 1.7 | 35.3 | 4.0 | 62.7 | 3.5 | |

2. Bold text indicates decreased activity exceeding 25% of matched control values

Example 11—Fractionation and Secondary Screening of *Cladophora sericea* (C.S.) Crude Extract To evaluate C.S. crude extract and select fractions for biological activity in anti-cancer assay, the following was undertaken:
1) Conduct secondary bio-assay screening to confirm activity of CS extract;
2) Fractionate CS extract and evaluate these fractions in biological assays;
3) Sub-fractionate fractions from CS extract identified in the secondary screening phase and evaluate these fractions in biological assays.
4) Acquire information on the group of chemicals responsible for bioactivity and identify bioactive markers for standardization of extract and product formulation.

11.1 Experimental Design

Extract Preparation:

Stock solution of the crude extract was prepared in dimethylsulfoxide (DMSO) at 10 mg/ml and stored in 200 µl aliquots at −20° C. until use. This preparation ensured that the DMSO content delivered to cells in culture never exceeded 1%.

CIMA Assay:

The effects of test extract was assessed following chronic exposure conditions in which cells were seeded at 2×10$^3$ cells/well (96 well plate) and incubated with test compounds for 72 h. Each fraction was evaluated over a range of six concentrations (0, 1, 10, 25, 50, or 100 µg/ml) where sufficient material was available and 50% lethal doses (LD$_{50}$) established if warranted. Cell proliferation was initially assessed using a standard colorimetric indicator of metabolic activity (CIMA) assay. In this assay, tetrazole reduction was evaluated as a measure of metabolic function that evaluates mitochondrial activity to determine the extent of cell proliferation within a culture. This assay is based on the reduction of yellow tetrazolium salt to purple formazan by mitochondrial reductases enzymes in viable cells, resulting in a colour change that confers a change in absorbance ($\lambda$=500-600 nm). Five human cell lines were selected for evaluation: U373 (glioblastoma-astrocytoma), THP1 (acute monocytic leukemia), MCF7 (mammary gland adenocarcinoma), SKOV3 (ovarian adenocarcinoma) and CCD1079SK (primary human fibroblasts) cells.

Fractionation Strategy:

Crude C.S. extract was fractionated as detailed in the diagram from FIG. 2. Briefly, primary extracts were initially fractionated into 5 fractions by C-18 column separation according to the protocol detailed in Example 1.

11.2 Fractionation and Analysis.

CS crude extract (0.5 g) was initially fractionated into 5 fractions by C-18 SPE column separation using 15 ml each of 5% MeOH (fraction 1), 25% MeOH (fraction 2), 50% MeOH (fraction 3), MeOH (fraction 4) and MeOH:CH$_2$Cl$_2$ (1:1) (fraction 5). The amounts obtained from this strategy are summarized in Table 15.

TABLE 15

| CS extract Fractions | Yield (mg) |
|---|---|
| F1 | 38 |
| F2 | 7 |
| F3 | 23 |
| F4 | 294 |
| F5 | 176 |

11.3 Results

CIMA Evaluation of Crude Extract

C.S. crude extract exhibited high activity and LD$_{50}$ values that could be calculated. This data is summarized in Table 16.

Evaluation of CS Crude Extract by CIMA

Cells were seeded in 96 well plates and incubated with the indicated concentration of CS primary extract for 72 h prior to CIMA assay. Equivalent concentrations of DMSO vehicle alone served as controls for each test concentration. Mean absorbance values from triplicate wells were expressed as percent changes relative to DMSO vehicle. Values are expressed as percent viability+standard deviation. Decreases exceeding 25% relative to controls were considered significant (red). Where sufficient inhibition of cell viability/proliferation was observed to support analysis, 50% lethal doses (LD$_{50}$) are indicated in µg/ml.

Several C.S. fractions were active. Particularly, fractions F4 and F5 were significantly active across a broad range of cell types. More particularly, fraction F4 was highly active across a broad range of cell types.

TABLE 16

Evaluation of C.S. crude extract fractions 1 to 5 by CIMA
*Cladophora sericea*

| | Conc. (μg/ml) | SKOV3 AVG | SD | MCF7 AVG | SD | U373 AVG | SD | THP-1 AVG | SD | CCD1079SK AVG | SD |
|---|---|---|---|---|---|---|---|---|---|---|---|
| F1 | 1 | 91.2 | 6.8 | 88.1 | 7.2 | 97.2 | 9.9 | 83.3 | 4.9 | 101.6 | 0.4 |
| | 10 | 86.1 | 6.7 | 71.8 | 10.2 | 98.1 | 6.1 | 83.6 | 6.7 | 99.3 | 5.8 |
| | 25 | 92.0 | 4.4 | 70.4 | 10.2 | 122.7 | 3.7 | 80.7 | 3.6 | 93.6 | 5.0 |
| | 50 | 82.2 | 4.9 | 68.0* | 8.4 | 106.0 | 12.0 | 78.3 | 4.6 | 98.9 | 7.7 |
| | 100 | 81.6 | 3.0 | 62.5* | 8.9 | 101.5 | 5.3 | 78.4 | 7.2 | 93.1 | 1.3 |
| | LD$_{50}$ | — | | — | | — | | — | | — | |
| F2 | 1 | 86.3 | 4.7 | 88.9 | 1.6 | 103.8 | 10.6 | 90.1 | 6.9 | 98.6 | 2.4 |
| | 10 | 81.9 | 0.5 | 83.8 | 1.4 | 95.3 | 5.7 | 92.9 | 7.1 | 93.5 | 3.2 |
| | 25 | 84.1 | 4.4 | 80.4 | 5.5 | 110.9 | 13.3 | 88.8 | 5.1 | 91.6 | 2.4 |
| | 50 | 79.5 | 5.6 | 78.0 | 4.5 | 98.3 | 12.1 | 88.9 | 8.0 | 92.1 | 8.9 |
| | 100 | 80.6 | 8.2 | 77.8 | 8.2 | 112.4 | 16.5 | 83.8 | 6.0 | 66.5 | 6.7 |
| | LD$_{50}$ | — | | — | | — | | — | | 79.5 | |
| F3 | 1 | 96.5 | 0.6 | 104.0 | 12.4 | 90.7 | 7.7 | 94.9 | 6.2 | 99.7 | 8.6 |
| | 10 | 89.8 | 3.7 | 89.3 | 3.3 | 90.6 | 6.7 | 96.9 | 3.1 | 95.9 | 4.9 |
| | 25 | 90.5 | 6.7 | 103.6 | 15.1 | 93.6 | 3.0 | 99.2 | 13.0 | 94.9 | 4.3 |
| | 50 | 86.3 | 9.8 | 95.3 | 10.4 | 83.9 | 6.4 | 94.6 | 7.2 | 93.7 | 1.6 |
| | 100 | 85.3 | 15.4 | 95.8 | 13.6 | 86.6 | 2.6 | 86.7 | 2.4 | 90.8 | 0.5 |
| | LD$_{50}$ | — | | — | | — | | — | | — | |
| F4 | 1 | 87.7 | 1.4 | 95.6 | 6.2 | 97.2 | 5.2 | 95.7 | 3.6 | 96.6 | 2.1 |
| | 10 | 75.2 | 3.3 | 85.2 | 12.3 | 92.4 | 10.5 | 92.9 | 4.1 | 90.5 | 4.5 |
| | 25 | 79.9 | 3.0 | 89.2 | 8.3 | 95.3 | 3.1 | 96.6 | 3.5 | 88.1 | 2.7 |
| | 50 | 83.3 | 7.7 | 53.2 | 5.4 | 71.2 | 3.2 | 95.4 | 6.2 | 75.4 | 2.6 |
| | 100 | 29.1 | 3.5 | 23.8 | 1.1 | 48.2 | 4.9 | 45.0 | 2.4 | 37.8 | 3.1 |
| | LD$_{50}$ | 77.4 | | 63.2 | | 96.7 | | — | | 84.5 | |
| F5 | 1 | 92.5 | 4.4 | 87.6 | 6.3 | 90.4 | 1.5 | 84.4 | 6.2 | 92.3 | 1.5 |
| | 10 | 67.6# | 1.1 | 82.2 | 3.5 | 73.5* | 3.7 | 78.0 | 8.7 | 73.8≠ | 2.3 |
| | 25 | 56.1# | 1.3 | 81.8 | 4.5 | 67.6* | 3.8 | 79.7 | 9.4 | 68.4* | 1.3 |
| | 50 | 46.1# | 4.6 | 63.9 | 9.7 | 61.7# | 4.6 | 89.5 | 9.3 | 66.7* | 4.4 |
| | 100 | 32.3# | 3.9 | 48.3 | 4.7 | 68.7* | 3.2 | 83.3 | 10.9 | 67.1* | 1.7 |
| | LD$_{50}$ | 33.1 | | 93.3 | | — | | — | | — | |

Figure 9:
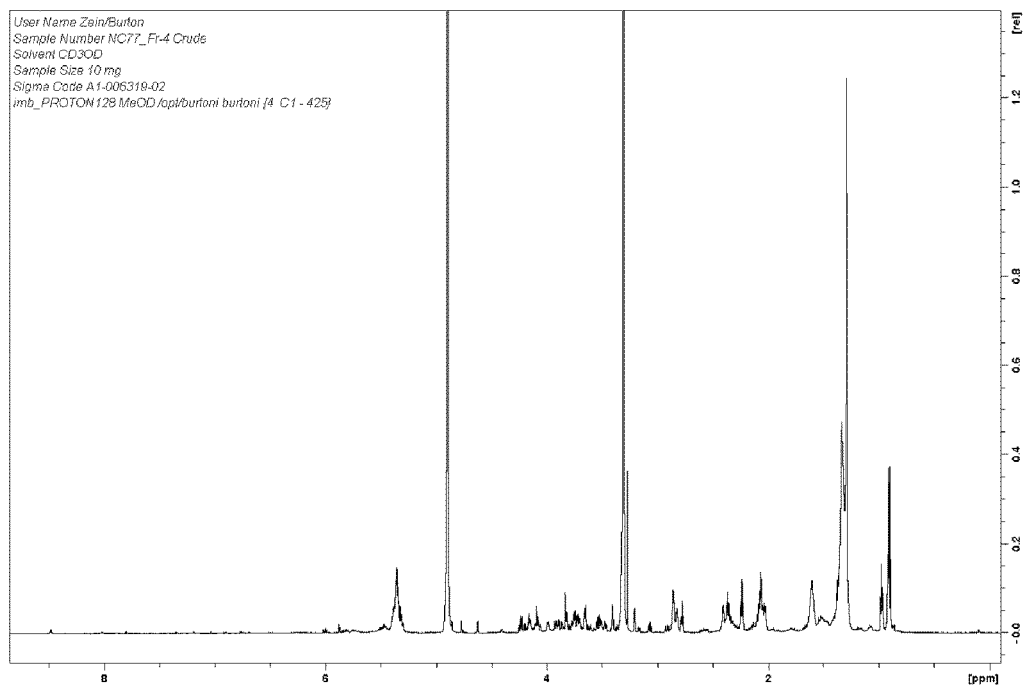
FIG. 9. Proton-NMR profiling of fraction NC77-4 from CC.
Figure 10:
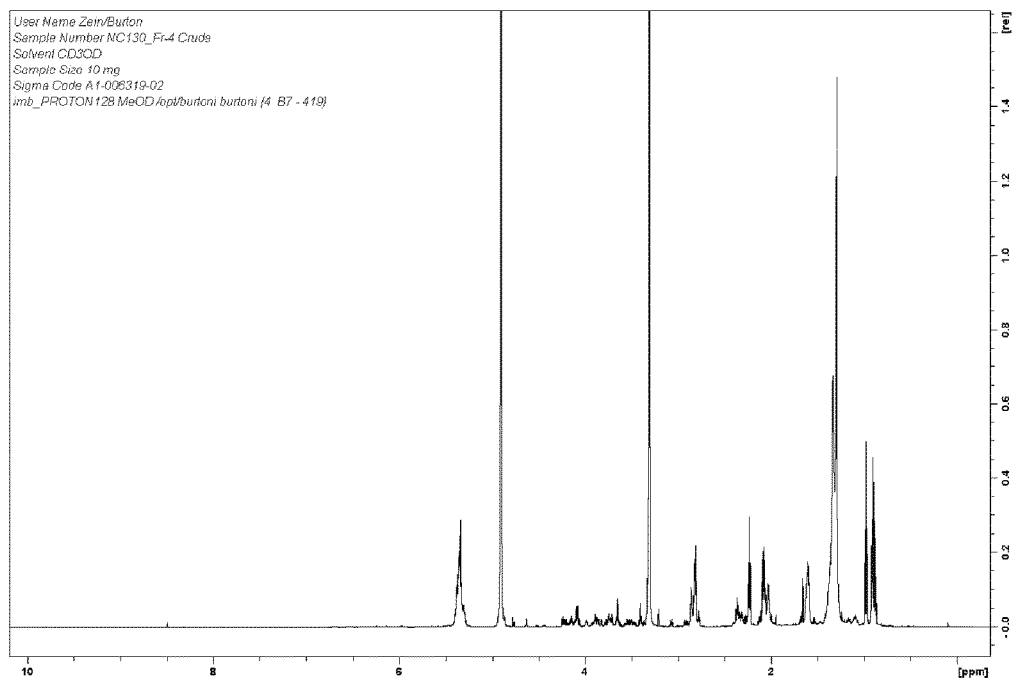
FIG. 10. Proton-NMR profiling of fraction NC130-4 from CS.

1. Bold text indicates decreased activity exceeding 25% of matched control values
2. #p < 0.001, *p < 0.01, ≠p < 0.05
3. —, LD$_{50}$ > 100 μg/ml Example 12. Analytical Profiling In the anti-cancer analysis, C.C. extract #77 fraction-4 (Table 12) and C.S. extract F-4 (Table 16) exhibited strong activity. These fractions were subjected to NMR analysis in order to provide insight into its composition as shown in FIGS. 9 and 10. Evaluation of the four dominant peaks in the spectra for 77-4 and C.S. F-4 both revealed the presence of —CH=CH— (about 5.4) and —CH$_2$—CH$_2$— (about 2.8-2.9 and about 2.0-2.3) chains indicative of predominantly unsaturated fatty acid species.

REFERENCES

Bellamy W T. Prediction of response to drug therapy of cancer. A review of in vitro assays. 1992. Drugs. 44:690-708.
Mosmann T. Rapid colorimetric assay for cellular growth and survival: application to proliferation and cytotoxicity assays. 1983. J Immunol Methods. 65: 55-63.
Niles A L, et al. A homogeneous assay to measure live and dead cells in the same sample by detecting different protease markers. Anal Biochem. 366:197-206

The invention claimed is:
1. A method of inhibiting growth of a cancer cell comprising contacting said cell with a growth-inhibiting concentration of a composition comprising a solvent extract from a seaweed selected from: *Chaetomorpha Cannabina* (CC) or *Cladophora sericea* (CS), wherein said solvent is aqueous ethanol.

2. The method of claim 1, wherein said solvent is about 80% aqueous ethanol.

3. The method of claim 2, wherein said seaweed is *Chaetomorpha Cannabina* (CC).

4. The method of claim 2, wherein said seaweed is *Cladophora sericea* (CS).

5. The method of claim 1, said composition being previously defatted with hexane.

6. The method of claim 1, said composition comprising a C-18 column methanol fraction from the extract.

7. The method of claim 6, wherein said composition is in dried form or in solution.

8. The method of claim 1, said composition comprising a C-18 column MeOH:CH$_2$Cl$_2$ (1:1) fraction from the extract.

9. The method of claim 8, wherein said composition is in dried form or in solution.

10. The method of claim 1, said composition being in dried form or in solution.

11. A method for the prevention or treatment of cancer in a mammal comprising administering a cancer growth-inhibiting concentration of a composition comprising a solvent extract from a seaweed selected from: *Chaetomorpha Cannabina* (CC) or *Cladophora sericea* (CS) to said mammal, wherein said solvent is aqueous ethanol.

12. The method of claim 11, wherein said composition is incorporated into an oral formulation for ingestion by said mammal.

13. The method of claim 12, wherein said oral formulation is a nutraceutical or nutritional formulation.

14. The method of claim 11, said composition being in admixture with a physiologically acceptable excipient.

15. The method of claim 14, wherein said excipient is suitable for oral administration, and said composition is for oral administration to said mammal.

16. The method of claim 15, wherein the oral formulation is in the form of a tablet, a capsule, a caplet, a powder or a syrup.

17. The method of claim 11, wherein said solvent is about 80% aqueous ethanol.

* * * * *